United States Patent [19]

Merianos

[11] Patent Number: 5,196,135
[45] Date of Patent: Mar. 23, 1993

[54] ANTIMICROBIAL, LOW TOXICITY, BLEND COMPOSITION OF BIS-QUATERNARY AMMONIUM COMPOUNDS

[75] Inventor: John J. Merianos, Middletown, N.J.

[73] Assignee: ISP Investments Inc., Wilmington, Del.

[21] Appl. No.: 772,182

[22] Filed: Oct. 7, 1991

[51] Int. Cl.$^5$ .......................... C11D 3/48; C11D 1/18; A01N 33/12; C07C 211/00

[52] U.S. Cl. ................................. 252/106; 252/547; 514/642; 564/295

[58] Field of Search ................ 252/106, 547; 514/642; 564/295

[56] References Cited

U.S. PATENT DOCUMENTS 4,110,263  8/1978  Lindemann et al. ........ 252/DIG. 13

OTHER PUBLICATIONS

Merianos, John J., *Disinfectants, Sterilization, and Preservatives,* Lea & Febiger Pub., (4th ed. 1991) pp. 225-255.
Chemical Abstract No. CA110(3):23322k, (1989) pp. 498-499.
Chemical Abstract No. CA109(11):92230v, (1988) p. 637.

*Primary Examiner*—Anthony McFarlane
*Assistant Examiner*—Nhat D. Phan
*Attorney, Agent, or Firm*—Walter Katz; Marilyn J. Maue; Joshua J. Ward

[57] ABSTRACT

An antimicrobial, low toxicity blend composition of several bis-quaternary ammonium compounds of defined structure, and in defined amounts of the composition, is described herein.

7 Claims, No Drawings

ANTIMICROBIAL, LOW TOXICITY, BLEND COMPOSITION OF BIS-QUATERNARY AMMONIUM COMPOUNDS

BACKGROUND OF THE INVENTION

1. Field of the Invention

This invention relates to antimicrobial compounds, and, more particularly, to a blend of such compounds having enhanced antimicrobial activity.

2. Description of the Prior Art

Bisquaternary ammonium compounds, such as acrylic alkyleneoxylated bisquaternary ammonium compounds, have been formulated into shampoo and cosmetic cleansing compounds as mildness additives for the detergents therein; see U.S. Pat. No. 4,110,263. However, for these and other applications, where the antimicrobial properties of such compounds are utilized, it is desired to provide compositions containing such compounds having enhanced antimicrobial activity.

Accordingly, it is an object of the present invention to provide a blend of bisquaternary ammonium compounds having enhanced antimicrobial activity as compared to the individual compounds therein.

A particular object herein is to provide a blend of defined bisquaternary ammonium compounds having a predetermined HLB value for antimicrobial use.

These and other objects and features of the invention will be made apparent from the following description herein.

SUMMARY OF THE INVENTION

What is provided herein is a defined antimicrobial blend composition of bis-quaternary ammonium compounds selected from those represented by the

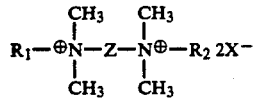

in which
Z is $-(CH_2CH_2O)_nCH_2CH_2-$
where n is 1 or 2; or
$-CH_2CH=CH-CH_2-$; and
$R_1$ and $R_2$ are independently $C_{12}$ or $C_{14}$-alkyl;
in the weight ratio of about
- 25% of the compound where both $R_1$ and $R_2$ are $C_{12}$-alkyl;
- 50% of the compound where $R_1$ is $C_{12}$-alkyl and $R_2$ is $C_{14}$-alkyl; and
- 25% of the compound where both $R_1$ and $R_2$ are $C_{14}$-alkyl;

the stated weight percents being ±20%; and $X^-$ is a halogen such as Cl, Br or I.

The thus-defined blend composition exhibits enhanced antimicrobial activity, and is less toxic, compared to the individual compounds in the composition.

In the preferred embodiment of the invention, Z is $-(CH_2CH_2O)_2$ and n is 2.

DETAILED DESCRIPTION OF THE INVENTION

The bis-quaternary ammonium compounds used to prepare the blend composition of the invention are made by reacting one mole of a dihalo compound selected from:
$XCH_2CH_2OCH_2CH_2X$,
$XCH_2CH_2OCH_2CH_2OCH_2CH_2X$ and
$XCH_2CH=CHCH_2X$;
where X is a halide such as Cl, Br and I, with 2 moles of dodecyldimethyl amine, tetradecyldimethylamine or predetermined mixtures thereof.

A typical reaction is the following:

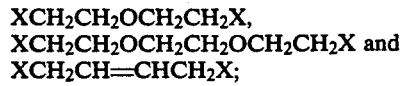

The blend compositions of the invention usually are prepared by refluxing the selected dichloro compound, the amines and an alkali metal halide, in alcoholic solution, removing the solvent, and adding a suitable organic solvent to precipitate the blend of bisquats in substantially quantitative yield.

A reaction mixture of one mole of dodecyldimethylamine, one mole of the tetradecyldimethylamine and one mole of the dichloro compound will provide the blend composition D as a mixture of three individual compounds, A, B and C, in defined amounts of each, as shown below.

BLEND COMPOSITION D

Compound A

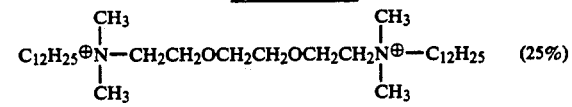

(25%)

Compound B

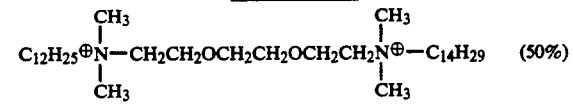

(50%)

Compound C

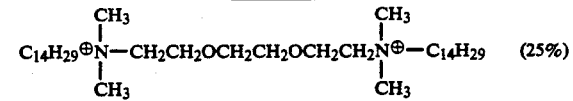

(25%)

where the stated percentages are ±20%, usually about ±5-10%. Of course, by varying the relative amounts of starting materials, a blend composition of different percentages of the individual compounds may be obtained.

These blend compositions exhibit an enhanced antimicrobial activity and reduced toxicity as compared to the individual compounds therein.

The antimicrobial blend compositions of the invention may be used per se, or, preferably admixed with an inactive or inert component to prepare pharmaceutical formulation such as powders, solutions, lotions, suspensions and the like. Typical additives include water, alcohols, starch, and the like. Other active ingredients may be included if desired.

Typical antimicrobial activities, represented by their Minimum Inhibitory Concentration (MIC) against E.-Coli, a gram negative microorganism, is presented in the Table below for both the individual compounds in blend composition D and the blend composition itself with different relative amounts of the A, B and C compounds therein (as measured in a 10% active solution).

TABLE

| Compound or Blend | MIC |
|---|---|
| A compound in D blend | 100 |
| B compound in D blend | 50 |
| C compound in D blend | 125 |
| D blend of 25A/50B/25C composition | 5 |
| D blend of 40A/20B/40C composition | 35 |
| D blend of 33A/33B/33C composition | 30 |
| D blend of 10A/80B/10C composition | 25 |

The MIC values of the D blend compositions in the TABLE are up to 25 times more favorable than the individual compounds in the blend.

The $LD_{50}$ toxicity of the blend composition D above, also is observed to be reduced by a factor of 5–6 as compared to the individual compounds. The invention will now be illustrated by the following example.

EXAMPLE 1

Preparation of Blend Composition D

A reaction solution of:
1,2-bis(2-chloroethoxy) ethane 37.5 g., 0.2 mole;
Dodecyldimethylamine 42.6 g., 0.2 mole;
Tetradecyldimethylamine 48.4 g., 0.2 mole;
Potassium Iodide 5 g.; and
Methanol 200 g., was mixed well and heated to 90°–100° C. for 12 hours. Then the solvent was removed to give a heavy syrupy residue which was treated with acetone to precipitate out the bisquats of the D blend composition in a yield of at least 95%. The blend composition comprised 25% by weight of A, 50% by weight of B and 25% by weight of C compounds.

While the invention has been described with particular reference to certain embodiments thereof, it will be understood that changes and modifications may be made which are within the skill of the art. Accordingly, it is intended to be bound only by the following claims, in which:

What is claimed is:

1. An antimicrobial, low toxicity blend composition of bis-quaternary ammonium compounds having the formula:

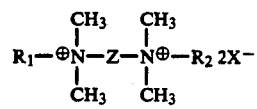

in which
Z is $-CH_2CH_2O)_nCH_2CH_2-$
where n is 1 or 2; and
$R_1$ and $R_2$ are independently $C_{12}$ or $C_{14}$-alkyl;
in the weight ratio of about
25% by weight of the compound where both $R_1$ and $R_2$ are $C_{12}$-alkyl;
50% by weight of the compound where $R_1$ is $C_{12}$-alkyl and $R_2$ is $C_{14}$-alkyl; and
25% by weight of the compound where both $R_1$ and $R_2$ are $C_{14}$-alkyl;
the stated weight percents being ±20%; and $X^-$ is a halogen such as Cl, Br or I.

2. A composition according to claim 1 wherein Z is $-CH_2CH_2O)_nCH_2CH_2-$.

3. A composition according to claim 2 wherein n is 2.

4. A composition according to claim 2 wherein n is 1.

5. A composition according to claim 1 where $X^-$ is Cl or Br.

6. A composition according to claim 1 wherein said percentages are ±5–10%.

7. A composition according to claim 1 which includes an inert component.

* * * * *